US00PP37145P2

(12) United States Plant Patent
Holtmaat

(10) Patent No.: US PP37,145 P2
(45) Date of Patent: Dec. 9, 2025

(54) ***SEDUM* PLANT NAMED 'PPF095'**

(50) Latin Name: ***Sedum* hybrid**
Varietal Denomination: PPF095

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 19/177,624

(22) Filed: Apr. 13, 2025

(51) Int. Cl.
*A01H 5/12* (2018.01)
*A01H 6/32* (2018.01)

(52) U.S. Cl.
USPC ..... Plt./479

(58) Field of Classification Search
USPC ..... Plt./479
See application file for complete search history.

(56) References Cited

U.S. PATENT DOCUMENTS

PP24,603 P2 * 7/2014 Hansen ..... A01H 5/02
Plt./479

* cited by examiner

*Primary Examiner* — Susan McCormick Ewoldt
(74) *Attorney, Agent, or Firm* — Penny J. Aguirre

(57) ABSTRACT

A new cultivar of *Sedum* plant named 'PPF095' that is characterized by its short plant height, its sturdy plant habit, its floriferous blooming habit, its flowers that are red in color, and its slightly glossy, dark grey-purple-black color foliage.

3 Drawing Sheets

CROSS REFERENCE TO A RELATED APPLICATION

This application is co-pending with a U.S. Plant Patent Applications filed for plants derived from the same breeding program that is entitled Sedum Plant Named 'PPC093' (U.S. Plant patent application No. 19/177,619)*.

Botanical classification: *Sedum* hybrid.

Variety denomination: 'PPF095'.

BACKGROUND OF THE INVENTION

The present invention relates to a new and distinct cultivar of *Sedum* plant, botanically of hybrid origin and known as *Sedum* 'PPF095' referred to hereinafter by its cultivar name, 'PPF095'. The new cultivar of *Sedum* is a hardy herbaceous perennial grown for use as a landscape and container plant.

The new cultivar arose from an ongoing breeding program conducted by the Inventor in Zuidwolde, The Netherlands. The Inventor collected and sowed seeds from open pollination of numerous unnamed and unpatented proprietary *Sedum* plants from the Inventor's breeding program. The seeds were pooled prior to sowing, therefore the parentage of 'PPF095' is unknown. 'PPF095' was selected as a single unique plant from the resulting seedlings in August 2020.

Asexual propagation of the new cultivar was first accomplished under the direction of the Inventor by tissue culture using meristematic tissue in August 2020 in Heerhugowaard, The Netherlands. Asexual propagation by tissue culture and stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'PPF095' as a unique cultivar of *Sedum*.

1. 'PPF095' exhibits a short plant height.
2. 'PPF095' exhibits a sturdy plant habit.
3. 'PPF095' exhibits a floriferous blooming habit.
4. 'PPF095' exhibits flowers that are red in color.
5. 'PPF095' exhibits slightly glossy, dark grey-purple-black color foliage.

'PPF095' can be compared to *Sedum* cultivars 'Mojave Jewels Ruby', (not patented), 'Cherry Tart' (U.S. Plant Pat. No. 24,603), and 'PPC093'. 'Mojave Jewels Ruby' is similar to 'PPF095' in having red color flowers. 'Mojave Jewels Ruby' differs from 'PPF095' in having a taller plant height and darker purple-black color foliage. 'Cherry Tart' is similar to 'PPF095' in having a short plant height. 'Cherry Tart' differs from 'PPF095' in having darker colored foliage and darker colored flowers. 'PPC093' is similar to 'PPF095' in having a short plant height. 'PPC093' differs from 'PPF095' in having flowers that are yellow and grey-purple in color and stems and leaves that are lighter in color.

BRIEF DESCRIPTION OF THE DRAWINGS

The accompanying color photographs illustrate the overall appearance and distinct characteristics of the new *Sedum*. The photographs were taken of a plant 2 years in age as field grown in Zuidwolde, The Netherlands and placed in a 27-cm container for the photographs.

The photograph in FIG. 1 provides a side view of 'PPF095' in bloom.

Figure 1:
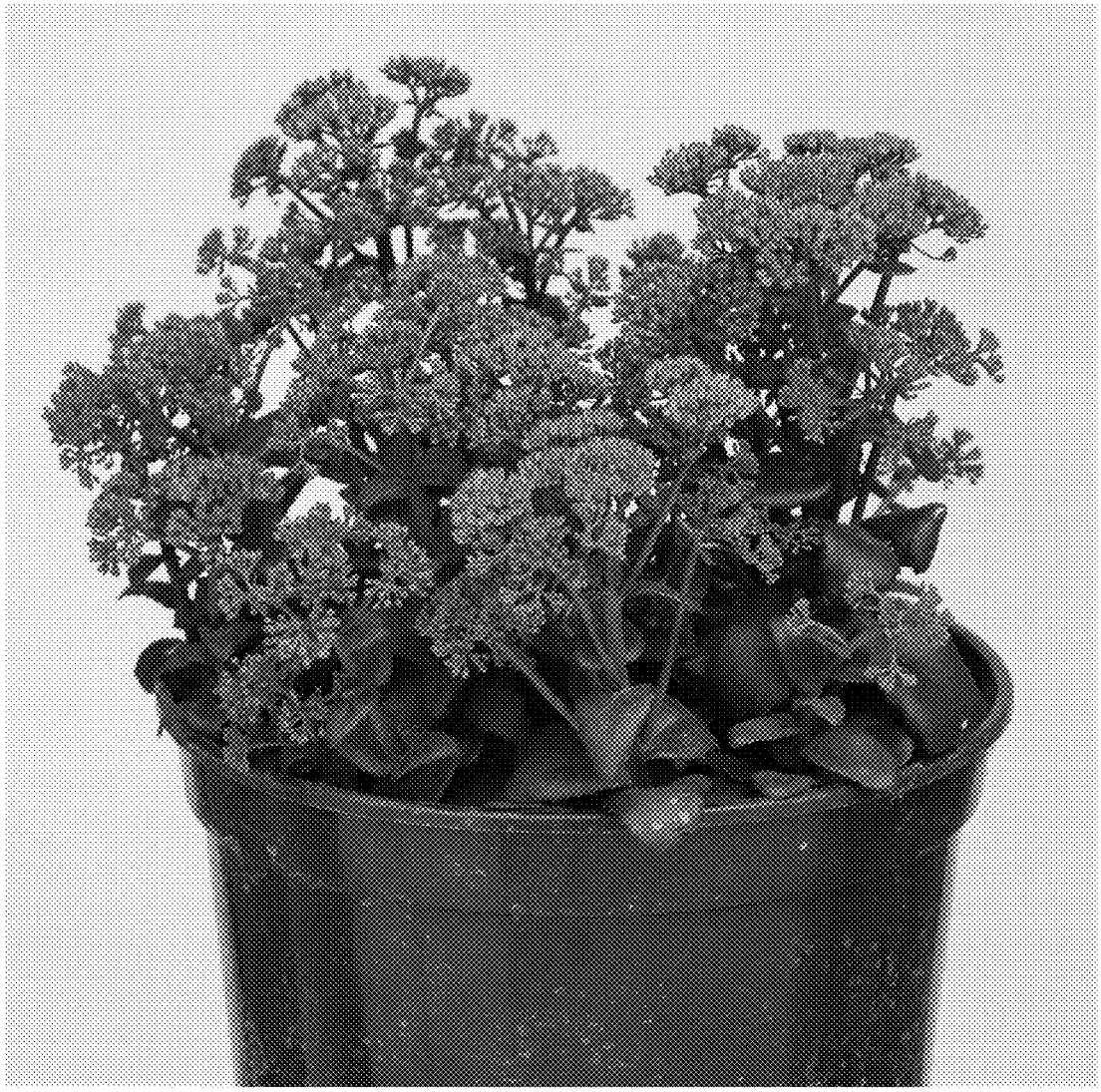
Figure 2:
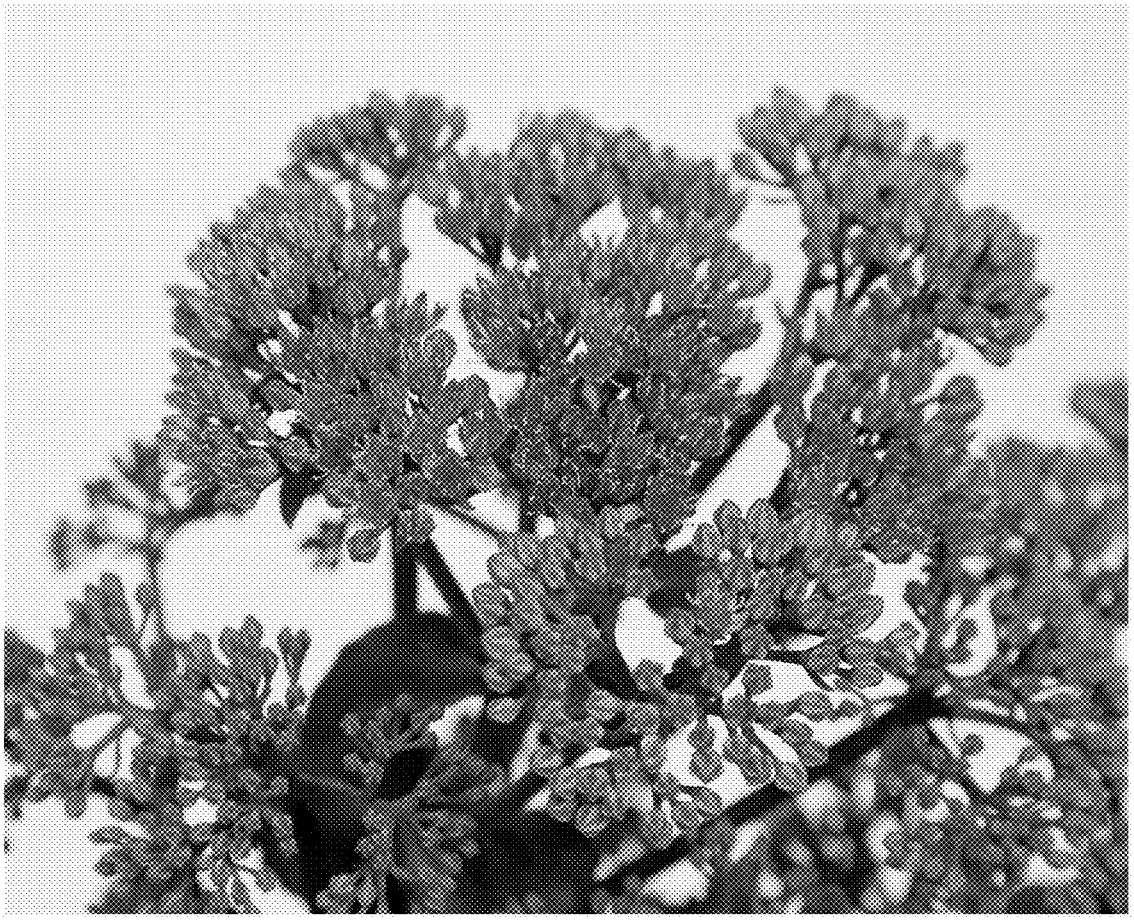

The photograph in FIG. 2 provides a view of the inflorescences of 'PPF095'.

Figure 3:
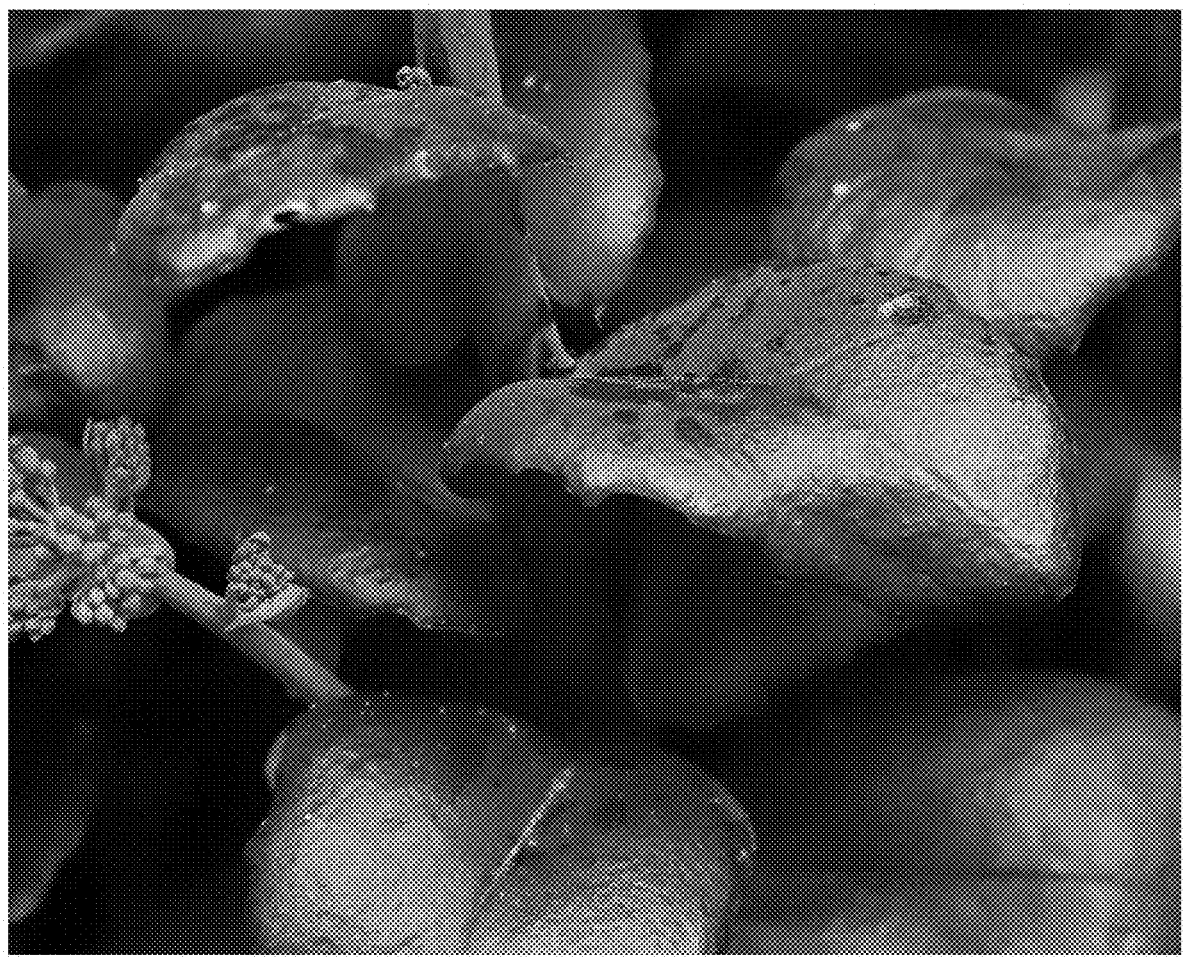

The photograph in FIG. 3 provides a close-up view of the foliage of 'PPF095'. The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on plants 2 years in age as field grown in Zuidwolde, The Netherlands and placed in 27-cm containers for the descriptions. The phenotype of the new cultivar may vary with variations in environmental, climatic, and cultural conditions, as it has not been tested under all possible environmental conditions. The color determination is in accordance with the 6th edition, 2019 reprint of the 2015 Colour Chart of the Royal Horticultural Society, London, England, except where general color terms of ordinary dictionary significance are used.

General Description:

*Blooming period*.—Spring to autumn in The Netherlands.

*Plant type*.—Herbaceous perennial.

*Plant habit*.—Short oblong to flattened, well-branched, short.

*Height and spread*.—Average of 25 cm in height and 35 cm in width as grown in the landscape.

*Hardiness*.—At least in U.S.D.A. Zones 5 to 9.

*Disease and pests*.—No susceptibility or resistance to diseases or pests has been observed.

*Root description*.—Fibrous, 155A.

*Propagation*.—Tissue culture (preferred) and stem cuttings.

*Growth rate*.—Moderately vigorous.

*Root development*.—Roots initiate in 6 weeks, a young plant can be produced in 2 months.

Stem Description:

*Stem shape*.—Rounded.

*Stem size*.—An average of 19 cm in length and 5 mm in width.

*Internode length*.—Average of 1.7 cm.

*Stem color*.—Young; 145B, very thin waxy layer N187B, mature; N186C, internodes 184A.

*Stem surface*.—Matte, young; 187C, very thin waxy layer N187B in color.

*Stem habit*.—Average angle of 20°, very strong, average of 24 main branches.

Foliage Description:

*Leaf shape*.—Ovate to oblong.

*Leaf division*.—Simple.

*Leaf arrangement*.—Opposite and alternate, occasionally in whorls of three.

*Leaf base*.—Truncate.

*Leaf apex*.—Broad bluntly acute to narrowly obtuse.

*Leaf venation*.—Pinnate, color upper surface 187A, color lower surface 152A.

*Leaf margins*.—Coarsely shallow dentate.

*Leaf attachment*.—Sessile.

*Leaf orientation*.—Outward.

*Leaf texture*.—Thick, succulent.

*Leaf surface*.—Both surfaces are smooth, glabrous, upper surface is slightly glossy, lower surface is matte.

*Leaf color*.—Young upper surface; a blend of N187A and 200A, covered with a very thin waxy layer N187C, young lower surface; N199A, fading slightly darker towards the margins N199B, covered with a very thin waxy layer N187C, mature upper surface; a blend of N186B and 203B, veins 187A, mature lower surface; a blend of 146A and 147A, slightly to strongly tinged N186C, covered with a very thin waxy layer N189C, veins 152A.

*Leaf size*.—Average of 5.2 cm in length, 2.9 cm in width.

Flower Description:

*Inflorescence type*.—Compound cyme.

*Inflorescence size*.—An average of 9.7 cm in diameter, 9.5 cm in height.

*Lastingness of inflorescence*.—At least one month, persistent.

*Flower type*.—Perfect, spreading, 5-starred.

*Flower number*.—An average of 375 flowers per inflorescence, 9,000 per plant.

*Flower fragrance*.—None.

*Flower buds*.—Ovate to nearly elliptic in shape, 4 mm length and 2.5 mm in width, glabrous and smooth surface, color; 183B, strongly tinged 150D, tip N186C.

*Flower size*.—6 mm in depth, 5.5 mm in diameter.

*Peduncles*.—Round in shape, strong, an average of 7.7 cm in length and 3 mm in diameter, surface is slightly glossy, color; 187B, sunny side 187A covered with a very thin waxy layer N187B, average angle of main peduncle 0°, average angle of secondary peduncles 35°.

*Pedicels*.—Round in shape, moderately strong, an average of 3 mm in length and 1 mm in diameter, surface is glossy, glabrous, smooth, color; 187B, sunny side darker; 187A covered with a thin waxy layer N187B terminal flower average of 0° to peduncle, pedicels of other flowers in an average angle of 20° to peduncle.

*Calyx*.—Rotate, 1.5 mm in length, 2.5 mm in width.

*Sepals*.—5, rotate, average of 1.5 mm in length, 1 mm in width, ovate in shape, entire margin, acute apex, broadly cuneate base, both surfaces matte, glabrous and smooth, color: when opening upper and lower surface; N187D, top N186A, when opening and fully open lower surface; 148D, strongly tinged and striped 185D, tip N186B.

*Petals*.—5, whorled, 5 mm in length and 2 mm in width, narrowly ovate in shape, cuneate base, acute apex, surfaces are matte, glabrous, and smooth, entire margin, color: when opening and fully open upper surface; 69A and 69B, top 59C and 59D, when opening and fully open lower surface; 69A, strongly tinged darker, especially towards the top; 64C, veins on the fully open lower surface 64C, top 187A.

Reproductive Organs:

*Pistils*.—5, 1 mm in length, stigma; 0.2 mm diameter, pointed, 61A in color, style; 0.75 mm in length, 61A in color, ovary; 63B, base 160D in color.

*Stamens*.—5, filaments; 3 mm, N74D in color, anther; broadly ovate shaped, 0.5 mm in length, 0.4 mm in width, 202A in color, pollen; low to moderate in quantity, 4C in color.

*Fruit*.—Fruit and seed production has not been observed to date.

It is claimed:

1. A new and distinct variety of *Sedum* plant named 'PPF095' as described and illustrated herein.

* * * * *